(12) United States Patent
Tamada

(10) Patent No.: US 9,107,593 B2
(45) Date of Patent: Aug. 18, 2015

(54) BLOOD PRESSURE MEASUREMENT APPARATUS AND CONTROL METHOD FOR BLOOD PRESSURE MEASUREMENT APPARATUS

(71) Applicant: SEIKO EPSON CORPORATION, Tokyo (JP)

(72) Inventor: Natsumi Tamada, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 30 days.

(21) Appl. No.: 13/711,142

(22) Filed: Dec. 11, 2012

(65) Prior Publication Data

US 2013/0165780 A1 Jun. 27, 2013

(30) Foreign Application Priority Data

Dec. 27, 2011 (JP) .................................. 2011-285319

(51) Int. Cl.
  *A61B 6/00* (2006.01)
  *A61B 8/04* (2006.01)
  *A61B 8/06* (2006.01)
  *A61B 8/00* (2006.01)

(52) U.S. Cl.
  CPC ... *A61B 8/04* (2013.01); *A61B 8/06* (2013.01); *A61B 8/4227* (2013.01); *A61B 8/58* (2013.01)

(58) Field of Classification Search
  CPC ........ A61B 8/04; A61B 8/4227; A61B 5/021; A61B 5/022; A61B 5/026; A61B 8/06
  See application file for complete search history.

(56) References Cited

U.S. PATENT DOCUMENTS

2003/0191399 A1 10/2003 Muramatsu et al.
2004/0176692 A1 9/2004 Kario et al.

FOREIGN PATENT DOCUMENTS

| JP | 10-243929 A | 9/1998 |
| JP | 2004-261452 A | 9/2004 |
| JP | 2006-247193 A | 9/2006 |
| JP | 2008-183414 A | 8/2008 |

*Primary Examiner* — Unsu Jung
*Assistant Examiner* — Joel Lamprecht
(74) *Attorney, Agent, or Firm* — Global IP Counselors, LLP

(57) ABSTRACT

In an ultrasound blood pressure monitor 1, blood flow speed in a measurement target blood vessel of a patient is gauged using a blood flow speed sensor section. The blood pressure of the patient is estimated using a blood pressure estimation section on the basis of results of the gauging of the blood flow speed sensor section by referencing a correlation formula which is expressed by correlation characteristics of the blood pressure and the blood flow speed of the patient which was found in a first correction process. Along with this, the correlation formula is corrected using a first correction section by rederiving the correlation formula using measurement values which are continuously input from a tonometry blood pressure monitor. The correlation characteristics are corrected using a second correction section by modifying the correlation characteristics using a measurement value which is directly input from an oscillometric blood pressure monitor or a measurement value of the oscillometric blood pressure monitor which is input in accordance with a user operation.

13 Claims, 9 Drawing Sheets

821

| Characteristics Value Number | Contraction Phase Characteristics Value ||
|---|---|---|
| | Contraction Phase Blood Pressure | Contraction Phase Central Blood Flow Speed |
| s1 | Ps1 | Vs1 |
| s2 | Ps2 | Vs2 |
| s3 | Ps3 | Vs3 |
| ⋮ | ⋮ | ⋮ |

| Characteristics Value Number | Extension Phase Characteristics Value ||
|---|---|---|
| | Extension Phase Blood Pressure | Extension Phase Central Blood Flow Speed |
| d1 | Pd1 | Vd1 |
| d2 | Pd2 | Vd2 |
| d3 | Pd3 | Vd3 |
| ⋮ | ⋮ | ⋮ |

Fig. 6

BLOOD PRESSURE MEASUREMENT APPARATUS AND CONTROL METHOD FOR BLOOD PRESSURE MEASUREMENT APPARATUS

CROSS-REFERENCE TO RELATED APPLICATIONS

This application claims priority to Japanese Patent Application No. 2011-285319 filed on Dec. 27, 2011. The entire disclosure of Japanese Patent Application No. 2011-285319 is hereby incorporated herein by reference.

BACKGROUND

1. Technical Field

The present invention relates to an apparatus, which measures blood pressure of a patient, and the like.

2. Background Technology

As a method for measuring blood pressure without pressurizing, for example, a technique is proposed where a blood vessel dynamics index such as blood vessel diameter, blood flow speed, blood flow amount, and the like of a blood vessel of a living body obliteration portion is gauged using ultrasound and blood pressure is estimated using the blood vessel dynamics index.

In determining blood pressure at home, during a medical examination, or the like, typically, there are often cases where pressurized blood pressure measurement which uses an oscillometric method is used. However, it is known that blood pressure changes significantly during the day. As a result, it is not always the case that it is possible to correctly judge the state of health of a patient or the state of an ailment if only blood pressure at one point in time is observed when gauging.

In consideration of this problem, for example, a technique is disclosed in PTL1 which relates to gauging blood pressure with free movement in order to capture the variation in blood pressure such as during sleep which is not captured in normal gauging of blood pressure. In addition, a technique for gauging blood pressure is disclosed in PTL2 which uses a tonometry method as a technique for monitoring variation in blood pressure for each pulse.

Japanese Laid-open Patent Publication No. 2004-261452 (Patent Document 1) and Japanese Laid-open Patent Publication No. H10-243929 (Patent Document 2) are examples of the related art.

SUMMARY

Problems to Be Solved by the Invention

In the technique for gauging blood pressure with free movement which is disclosed in PTL1, it is necessary for a blood pressure monitoring body with a box shape to be fixed to the hip or the like of a patient and a cuff band which is connected with a tube for supplying air is normally mounted onto the hip of a patient and this is inconvenient in terms of performing daily activities. In addition, it is almost impossible in practice to perform pressurized gauging of blood pressure using the cuff continually in daily activities and it is not always the case that it is possible to realize appropriate blood pressure management.

In addition, in the blood pressure measurement technique which uses the tonometry method disclosed in PTL2, there is a characteristic such that it is possible to continuously record the blood pressure waveform for each pulse in a non-invasive manner. However, in this blood pressure measurement technique, since the measurement value changes in a sensitive manner due to the movement of the patient, there is a problem in that it is necessary for a resting state to be maintained during gauging and it is not suitable for long-term use.

The present invention is realized in consideration of the problems described above and has an advantage of proposing a novel technique where it is possible to capture variation in blood pressure by gauging blood flow speed.

Means Used to Solve the Above-Mentioned Problems

The first embodiment which solves the problems above is a blood pressure measurement apparatus which is provided with a blood flow speed gauging section which gauges blood flow speed in a measurement target blood vessel of a patient, a blood pressure estimation section which estimates blood pressure on the basis of the results of the gauging of the blood flow speed gauging section by referencing correlation characteristics of the blood pressure and the blood flow speed of the patient which have been set in advance, a first input section which is connected to a first external measurement apparatus which performs blood pressure measurement using a continuous method and continuously inputs measurement values of the first external measurement apparatus, a second input section which is connected to a second external measurement apparatus which performs gauging of blood pressure using an intermittent method and inputs a measurement value of the second external measurement apparatus or inputs a measurement value, which has been measured by the second external measurement apparatus, due to a user operation, a first correction section which corrects the correlation characteristics by rederiving the correlation characteristics using measurement values which are continuously input by the first input section, and a second correction section which corrects the correlation characteristics by modifying the correlation characteristics using the measurement value which is input by the second external input section.

In addition, as another embodiment, a control method of a blood pressure measurement apparatus can be configured to include gauging blood flow speed in a measurement target blood vessel of a patient, estimating blood pressure on the basis of the results of gauging by referencing correlation characteristics of the blood pressure and the blood flow speed of the patient which have been set in advance, correcting the correlation characteristics by rederiving the correlation characteristics using measurement values which are continuously input from a first external measurement apparatus by connecting to the first external measurement apparatus which performs gauging of blood pressure using a continuous method, and correcting the correlation characteristics by modifying the correlation characteristics using a measurement value which is measured by a second external measurement apparatus which performs gauging of blood pressure using an intermittent method.

According to the first embodiment, blood flow speed in a measurement target blood vessel of a patient is gauged using the blood flow speed gauging section. Then, blood pressure is estimated by the blood pressure estimation section on the basis of the results of the gauging of the blood flow speed gauging section by referencing the correlation characteristics of the blood pressure and the blood flow speed of the patient which have been set in advance. According to experiments which were performed by the present inventors, it is understood that there is a highly correlated relationship between the blood pressure and the blood flow speed of a patient. As a result, it is possible to capture variation in blood pressure using a simple configuration in which the correlation characteristics of the blood pressure and the blood flow speed of the patient are set in advance and the blood flow speed of the patient is gauged by referencing the correlation characteristics.

However, when the viscosity of the blood or the like in the measurement target blood vessel changes, the relationship of the blood pressure and the blood flow speed of the patient breaks down and the theoretical correlation characteristics change. As a result, correction of the correlation characteristics is necessary if the blood pressure estimation is to be continuously performed in daily activities. Therefore, there is a configuration which is provided with the first correction section which corrects the correlation characteristics by rederiving the correlation characteristics using the measurement values which are continuously input from the first input section which performs gauging of blood pressure using a continuous method and the second correction section which corrects the correlation characteristics by modifying the correlation characteristics using the measurement value which is directly input from the second external input section which performs gauging of blood pressure using an intermittent method or the measurement value of the second external measurement apparatus which is input in accordance with a user operation. Due to this, since it is possible to correct the correlation characteristics using the measurement values of the external measurement apparatuses which perform gauging of blood pressure using gauging methods which are different types, it is possible to correct the correlation characteristics by appropriately selecting the correction section according to the simplicity of the correction, whether there is an apparatus environment where correction is possible, and the like.

In addition, as a second embodiment, the blood pressure measurement apparatus in the blood pressure measurement apparatus of the first embodiment can be a configuration where the correlation characteristics are expressed by a formula with a plurality of parameters, the first correction section rederives the correlation characteristics by recalculating all of the values of the plurality of parameters, and the second correction section modifies the correlation characteristics by changing the values of a portion of the parameters out of the plurality of parameters.

According to the second embodiment, it is possible to finely perform the correction of the correlation characteristics since the first correction section rederives the correlation characteristics by recalculating all of the values of the plurality of parameters. On the other hand, it is possible to simplify the correction of the correlation characteristics since the second correction section corrects the correlation characteristics by changing the values of a portion of the parameters out of the plurality of parameters.

In addition, as a third embodiment, the blood pressure measurement apparatus in the blood pressure measurement apparatus of the first or second embodiments can be a configuration where a blood flow state determination section, which determines the blood flow state of the measurement target blood vessel using the results of the gauging of the blood flow speed gauging section, and a correction necessity determination section, which determines the necessity of correction of the correlation characteristics by comparing a reference blood flow state of the measurement target blood vessel which is set in advance and the blood flow state which is determined by the blood flow state determination section, are provided.

According to the third embodiment, the blood flow state of the measurement target blood vessel is determined by the blood flow state determination section using the results of the gauging of the blood flow speed gauging section. In addition, the necessity of correction of the correlation characteristics is determined by the correction necessity determination section by comparing a reference blood flow state of the measurement target blood vessel which is set in advance and the blood flow state which is determined by the blood flow state determination section. If the blood flow state which has been determined changes considerably in comparison to the reference blood flow state, there is a high possibility that the relationship between the blood pressure and the blood flow speed has also changed considerably. As a result, in this case, it is possible to determine whether correction of the correlation characteristics is necessary.

In addition, as a fourth embodiment, the blood pressure measurement apparatus in the blood pressure measurement apparatus of the third embodiment can be a configuration where the blood flow speed gauging section gauges the blood flow speed in a plurality of positions which are different positions in a diameter direction in the measurement target blood vessel and the blood flow state determination section determines the distribution or the change trend of the blood flow speed in a transverse direction of the measurement target blood vessel (referred to below comprehensively as "blood flow speed distribution") as the blood flow state using the results of the gauging of the blood flow speed gauging section.

According to the fourth embodiment, the blood flow speed in a plurality of positions which are different positions in a diameter direction in the measurement target blood vessel are gauged using the blood flow speed gauging section. Then, the blood flow speed distribution in a transverse direction of the measurement target blood vessel is determined as the blood flow state by the blood flow state determination section using the gauging result by the blood flow speed gauging section. The blood flow speed in a transverse direction of the measurement target blood vessel is different according to the position in the transverse direction. It is possible to appropriately determine the necessity of correction using the distribution or the change trend of the blood flow speed in the transverse direction of the measurement target blood vessel as the blood flow state.

In this case, as a fifth embodiment, it is possible for the blood pressure measurement apparatus in the blood pressure measurement apparatus of the fourth embodiment to be a configuration where the correction necessity determination section determines the necessity of correction of the correlation characteristics by comparing the undulations of the blood flow speed distribution of the reference blood flow state (referred to below as "reference undulations") and the undulations of the blood flow speed distribution which is determined using the blood flow state determination section (referred to below as "gauging undulations").

According to the fifth embodiment, the necessity of correction of the correlation characteristics is determined by the correction necessity determination section by comparing the reference undulations and the gauging undulations. When the blood flow state of the measurement target blood vessel changes considerably, the difference in the reference undulations and the gauging undulations increases. As a result, for example, it is possible to easily determine the necessity of correction of the correlation characteristics by setting the difference in the reference undulations and the gauging undulations as an index for judgment.

In addition, as a sixth embodiment, the blood pressure measurement apparatus in the blood pressure measurement apparatus of any of the third to the fifth embodiments can be a configuration where the correction necessity determination section determines whether correction using any of the first correction section or the second correction section is necessary based on the results of the comparison.

According to the sixth embodiment, whether correction using any of the first correction section or the second correction section is necessary is determined by the correction necessity determination section based on the results of the comparison. For example, in a case where the discrepancy between the reference blood flow state and the blood flow state which is determined by the blood flow state determination section is large as a result of the comparison, it is determined that correction using the first correction section is necessary in order to perform fine correction. Conversely, in a case where the discrepancy is small, it is determined that correction using the second correction section is necessary in order to perform a simple correction.

BRIEF DESCRIPTION OF THE DRAWINGS

Referring now to the attached drawings which form a part of this original disclosure:

FIG. 5 is a data configuration example of contraction phase characteristics value data;

FIG. 6 is a data configuration example of extension phase characteristics value data;

DETAILED DESCRIPTION OF EXEMPLARY EMBODIMENTS

1. General Structure

As an embodiment where the present invention is applied, an embodiment of a blood flow measurement apparatus which measures blood pressure of a patient will be described with the wrist of a patient as a measurement target portion and an artery of the measurement target as the radial artery. Here, naturally, the embodiments where it is possible for the present invention to be applied are not limited to the embodiment described below.

Figure 1A:
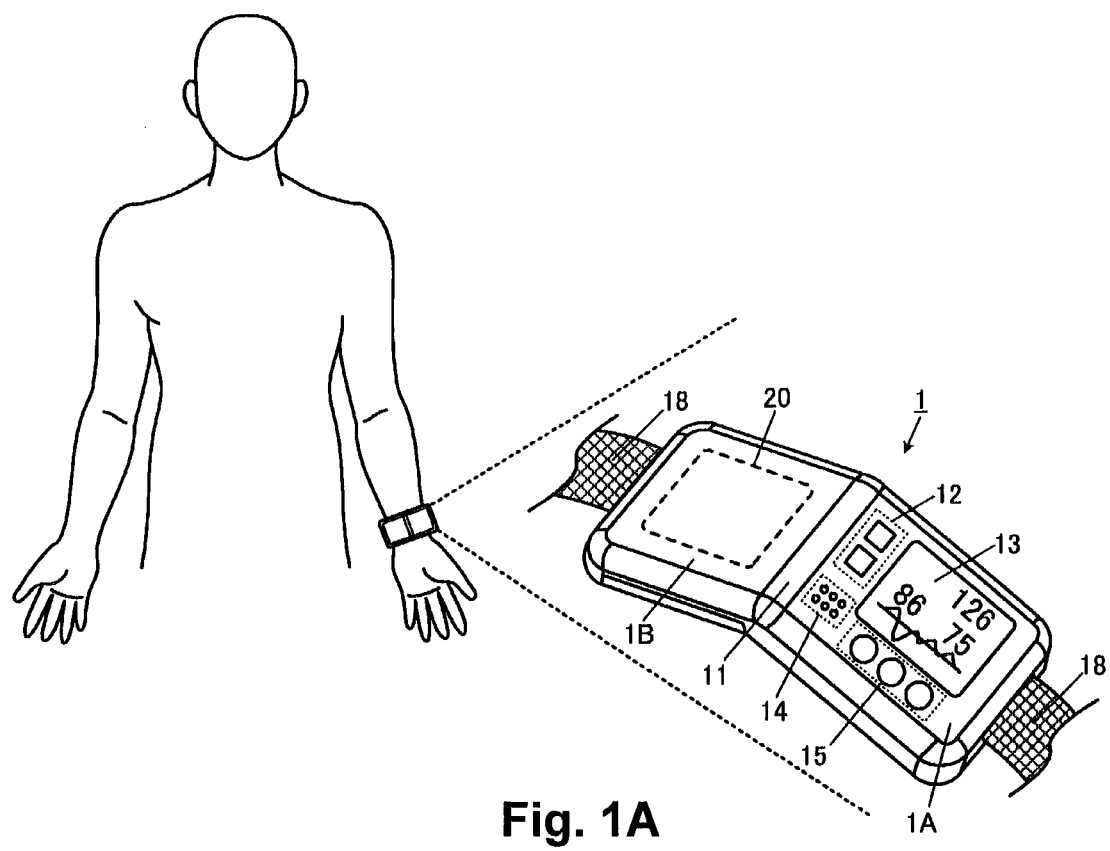
FIG. 1A is a schematic configuration diagram of an ultrasound blood pressure monitor.

FIG. 1A is a schematic diagram of an outer appearance of an ultrasound blood pressure monitor 1 which is a blood pressure measurement apparatus in the embodiment. The ultrasound blood pressure monitor 1 is configured so that a body section is able to be mounted onto a measurement target portion (in particular, a wrist) using a strip section 18. The strip section 18 is a mounting tool for mounting an apparatus body onto the measurement target portion of a patient and is configured to have a band which is provided with a surface fastener, a clip which is for pinching a gauging section, and the like. The body section of the ultrasound blood pressure monitor 1 is configured to be connected to a first portion 1A and a section portion 1B via a hinge section 11.

An operation button 12, a liquid crystal display device 13, a speaker 14, and a LED (Light Emitting Diode) lamp 15 are provided in the first portion 1A.

The operation button 12 is used for the patient to operate and input starting instructions for the measurement of blood pressure and various types of amounts which are related to the measurement of blood pressure.

The measurement results of the blood pressure using the ultrasound blood pressure monitor 1 is displayed in the liquid crystal display device 13. As the display method, a measurement value of the blood pressure can be displayed using a numerical value or there can be a display using a lamp or the like.

There is audio output such as various types of voice guidance which are related to the measurement of blood pressure from the speaker 14. In the embodiment, correction of the ultrasound blood pressure monitor 1 is performed using an external measurement apparatus (a tonometry blood pressure monitor 3 or an oscillometric blood pressure monitor 5). At this time, voice guidance which instructs the mounting of these blood pressure monitors and the like is output from the speaker 14

The LED lamp 15 emits light in three colors of, for example, red, yellow, and blue and is used in order to perform a predetermined notification which relates to the reliability of the blood pressure estimation results or notification which instructs of a correction with regard to the patient.

A blood flow speed sensor section 20 is provided in the second portion 1B. The blood flow speed sensor section 20 is a sensor which gauges the blood flow speed in the measurement target blood vessel of the patient using ultrasound.

The blood flow speed sensor section 20 transmits a pulse signal or a burst signal of ultrasound of several MHz to several tens of MHz from an ultrasound transmission section toward the measurement target blood vessel. Then, the blood flow speed in the measurement target blood vessel is gauged using, for example, an ultrasound Doppler method. In the embodiment, the blood flow speed sensor section 20 gauges the blood flow speed at a plurality of positions which are different positions in a diameter direction in the radial artery which is the measurement target blood vessel. Here, the description of the details of this is omitted since blood flow speed gauging methods which use an ultrasound Doppler method are known in the related art.

In addition, although omitted in the diagrams, a control substrate for comprehensively controlling the device is built into the body section of the ultrasound blood pressure monitor 1. A microprocessor, a memory, a circuit which is related to the sending and receiving of ultrasound, a built-in battery, and the like are mounted in the control substrate.

Figure 1B:
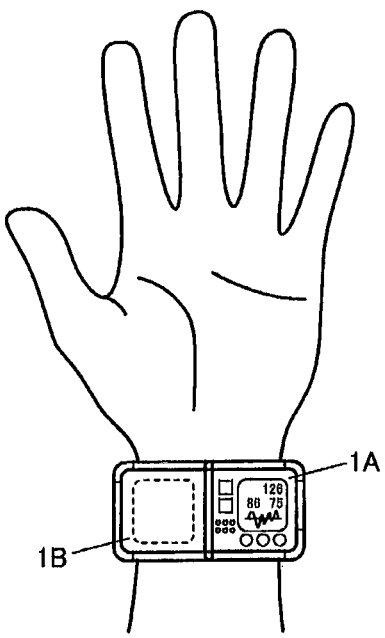
FIG. 1B is a state diagram in which an ultrasound blood pressure monitor is mounted.

FIG. 1B is a diagram illustrating a state where the ultrasound blood pressure monitor 1 is mounted onto the left wrist of the patient. As shown in FIG. 1B, the ultrasound blood pressure monitor 1 is mounted onto the wrist of the patient with a positioning so that the body section is directed to the inner side of the wrist. At this time, the second portion 1B where the blood flow speed sensor section 20 is provided is mounted so as to come to the thumb side of the wrist of the patient. This is so that the blood flow speed sensor section 20 is positioned directly above this with the measurement target blood vessel as the radial artery where there is flow to the thumb side of the wrist.

2. Principles

Figure 2:
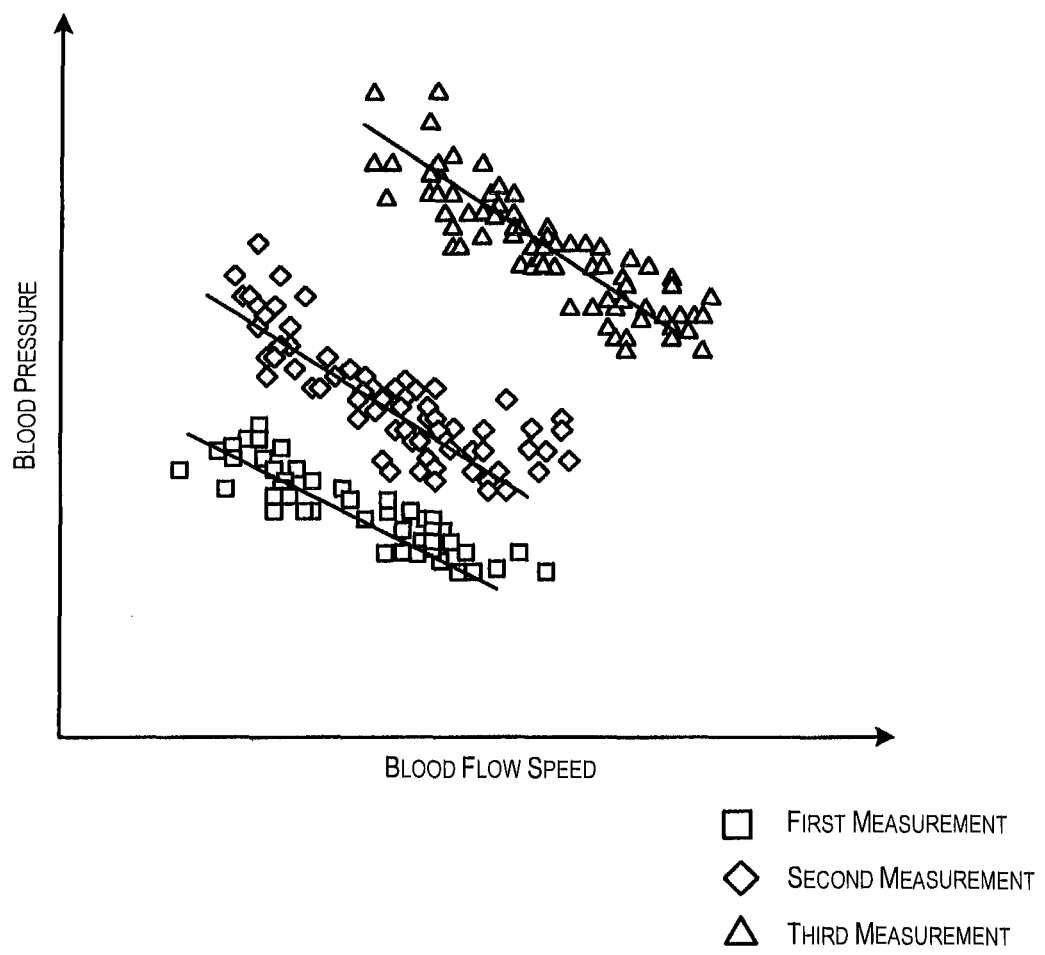
FIG. 2 is experiment results illustrating a correlation relationship of contraction phase blood flow speed and contraction phase blood pressure.

FIG. 2 is a diagram illustrating an example of experiment results where experiments were performed by the present inventors to adjust the correlation characteristics of the blood pressure and the blood flow speed which are gauged in the radial artery with one patient as the target. In FIG. 2, the horizontal axis indicates the blood flow speed and the vertical axis indicates the blood pressure. A total of three measurements (a first measurement to a third measurement) were performed with constant time intervals. In each of the measurements, the contraction phase blood pressure and the contraction phase blood flow speed were gauged for each pulse and characteristics values (coordinate values) where the blood pressure and the blood flow speed correspond were plotted on the coordinates. One plotting which is shown in the coordinates indicates the characteristics values of one pulse and the characteristics values which are obtained using the first measurement to the third measurement are respectively shown in the diagram by plotting with squares, diamonds, and triangles.

When viewing the experiment results, it is understood that there are negative correlation characteristics between blood flow speed and blood pressure. With regard to each of the measurements, linear approximation lines (linear regression lines) which are calculated using a least squares method, where the trend in the characteristic values of the blood flow speed and the blood pressure is a type of regression analysis process, are shown in the diagram in combination with the plotting. It is understood that the slope of the linear regression line is substantially constant for each of the measurements. However, it is understood that the overall sizes of the characteristics values are different for each of the measurements, and as a result, the linear regression line shifts up and down.

As a cause whereby such results are acquired, the problem portion has been described but it is thought that this is because of changes in the viscosity of the blood (blood viscosity) which flows in the radial artery. That is, since the blood viscosity changes over time, there is a concern that it is not possible to correctly estimate the blood pressure of the patient by using the constant and uniform correlation characteristics.

Therefore, in the embodiment, the blood flow state of the radial artery is determined using the results of the gauging of the blood flow speed sensor section 20. Then, the reliability of the estimation results of the blood pressure is determined by comparing a reference blood flow state of the measurement target blood vessel which is set in advance and the blood flow state which has been determined.

In the embodiment, a blood flow state which is determined during correction of the ultrasound blood pressure monitor 1 is set as the reference blood flow state. In the embodiment, two types of correction of a first correction, which uses the tonometry blood pressure monitor 3 where gauging of blood pressure is performed using a continuous method, and a second correction, which uses the oscillometric blood pressure monitor 5 where gauging of blood pressure is performed using an intermittent method, are performed. In these corrections, a correlation formula (linear regression line) which is expressed by the correlation characteristics of the blood pressure and the blood flow speed is corrected. In addition, the reference blood flow state is updated using the results of the gauging of the blood flow speed sensor section 20 during correction.

In the first correction, the correlation characteristics are corrected by rederiving the correlation characteristics using a measurement value of the blood pressure which is measured continuously using the tonometry blood pressure monitor 3. As described above, in the embodiment, the correlation characteristics are approximated using a correlation formula (linear regression line) which is expressed using a linear function. The correlation formula is expressed using a formula which has two parameters of the slope and intercept. In the first correction, the correlation formula is rederived by recalculating both of the two parameters. This is equivalent to rederiving the correlation characteristics by recalculating all of the values of the plurality of parameters in the formula which is expressed by the correlation characteristics.

On the other hand, in the second correction, the correlation characteristics are corrected by modifying the correlation characteristics using a measurement value of the blood pressure which is measured intermittently using the oscillometric blood pressure monitor 5. Specifically, the correlation formula is modified so that, out of the two parameters of the slope and the intercept of the correlation formula, only the intercept is changed without changing the slope. This is equivalent to modifying the correlation characteristics by changing a portion of the parameter values out of the plurality of parameters which express the correlation characteristics.

The first correction is referred to as a fine correction since it is a correction where the correlation characteristics are rederived by recalculating all of the values of the plurality of parameters which express the correlation characteristics. On the other hand, the second correction is referred to as a simple correction since it is a correction where the correlation characteristics are modified by changing a portion of the parameter values out of the parameters which express the correlation characteristics. The detailed methods of the first correction and the second correction will be described in detail using flow charts.

Figure 3:
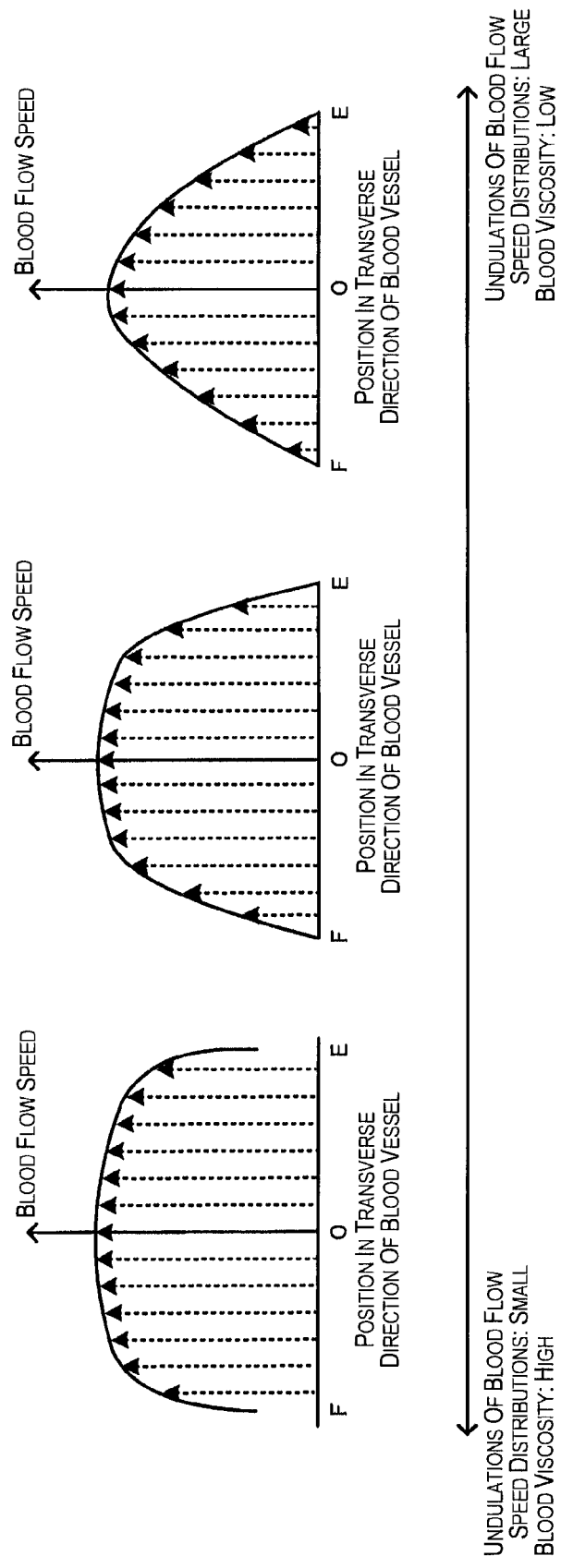
FIG. 3 is an explanatory diagram of a determination of reliability of blood pressure estimation results.

FIG. 3 is an explanatory diagram of a blood flow state determination method. The blood flow speed sensor section 20 gauges the blood flow speed at positions which are different in the diameter direction (transverse direction) of the radial artery. The distribution or the change trend of the blood flow speed in the transverse direction of the radial artery is determined as the blood flow state using the results of the gauging. The distribution or the change trend of the blood flow speed is referred to below comprehensively as "blood flow speed distribution".

In FIG. 3, three types of blood flow speed distributions are shown in the diagram. In each of the blood flow speed distributions, the horizontal axis indicates the position in the transverse direction of the radial artery. "O" is the center position of the blood vessel, "F" is the position of the wall in front of the blood vessel, and "E" is the position of the wall to the rear of the blood vessel. In addition, the vertical axis is the blood flow speed and indicates the size of the blood flow speed which is gauged using arrows which are represented by dotted lines.

The speed distribution of the blood which flows in the blood vessel changes according to the blood viscosity. As shown in FIG. 3, the undulations of the blood flow speed distribution falls as blood viscosity increases and the undulations of the blood flow speed distribution increases as blood viscosity falls.

Therefore, in the embodiment, the reliability of the blood pressure estimation results is determined based on the difference in the undulations of the blood flow speed distribution of the reference blood flow state (referred to below as "reference undulations") and the undulations of the blood flow speed distribution which has been determined (referred to below as "gauging undulations"). It is possible for the undulations of the blood flow speed distribution to be determined based on, for example, the gradient of the blood flow speed distribution.

More specifically, the gradient of the reference blood flow speed distribution (referred to below as "reference gradient") is calculated as reference undulations and is compared with the gradient of the blood flow speed distribution which has been determined (referred to below as "gauging gradient"). The gradient of the blood flow speed distribution is found as, for example, the difference in the blood flow speeds at positions which are adjacent in the transverse direction with regard to the blood flow speeds across all of the transverse direction of the radial artery which has been measured and an average of these is found.

In addition, as a different method, for example, a difference (or a ratio) of the blood flow speed at the center position "O" of the blood vessel, the position "F" of the wall before the blood vessel, and the position "E" of the wall to the rear of the blood vessel can be determined and these values can be set as the gradient of the blood flow speed distribution. Here, these gradient calculation methods are only examples, and naturally, other gradient calculation methods which are known in the related art can be adopted.

If the gradient is calculated as described above, a threshold is set with regard to the absolute value of the difference of the reference gradient and the gauging gradient (referred to below as "gradient difference") and the reliability of the blood pressure estimation results is determined to be low in a case where the absolute value of the gradient difference exceeds the threshold. The threshold with regard to the absolute value of the gradient difference is equivalent to the threshold condition of the reliability determination.

The current correlation characteristics are considerably deviated from the correlation characteristics which are found during correction as the different in the reference undulations (for example, the reference gradient) and the gauging undulations (for example, the gauging gradient) increases. As a result, it is possible for the reliability of the blood pressure estimation results to be determined as low as the difference in the reference undulations and the gauging undulations increases.

Therefore, the threshold conditions can be set so that the determination results of the reliability of the blood pressure estimation results are classified into multiple steps. For example, a first threshold and a second threshold which is larger than the first threshold are set as the thresholds with regard to the absolute values of the gradient difference. Then, for example, the reliability is determined as "high" in a case where the absolute value of the gradient difference is less than the first threshold, the reliability is determined as "medium" in a case of being equal to or more than the first threshold and less than the second threshold, and the reliability is determined as "low" in a case of being equal to or more than the second threshold.

Then, in the embodiment, whether correction of the correlation characteristics is determined in combination using the same technique as the reliability determination described above. That is, the necessity of correction of the correlation characteristics is determined by comparing the reference blood flow state of the measurement target blood vessel (for example, the reference blood speed distribution) and the blood flow state which has been determined (for example, the blood flow speed distribution).

Since the possibility that the blood viscosity has changed considerably increases as the difference in the reference undulations and the gauging undulations increases, it is necessary to more finely perform correction of the correlation characteristics. However, if the blood viscosity has not changed to a substantial extent, it is possible to consider that performing a simple correction is sufficient without performing fine correction.

Therefore, for example, the extent of the difference of the reference undulations and the gauging undulations is classified into three steps based on the same technique as the reliability determination described above. Then, it is determined that the first correction which is a fine correction is necessary in a case where the difference is "large" and it is determined that the second correction which is a simple correction is necessary in a case where the difference is "medium". In addition, it is determined that correction is not necessary in a case where the difference is "small".

3. Functional Configuration

Figure 4:
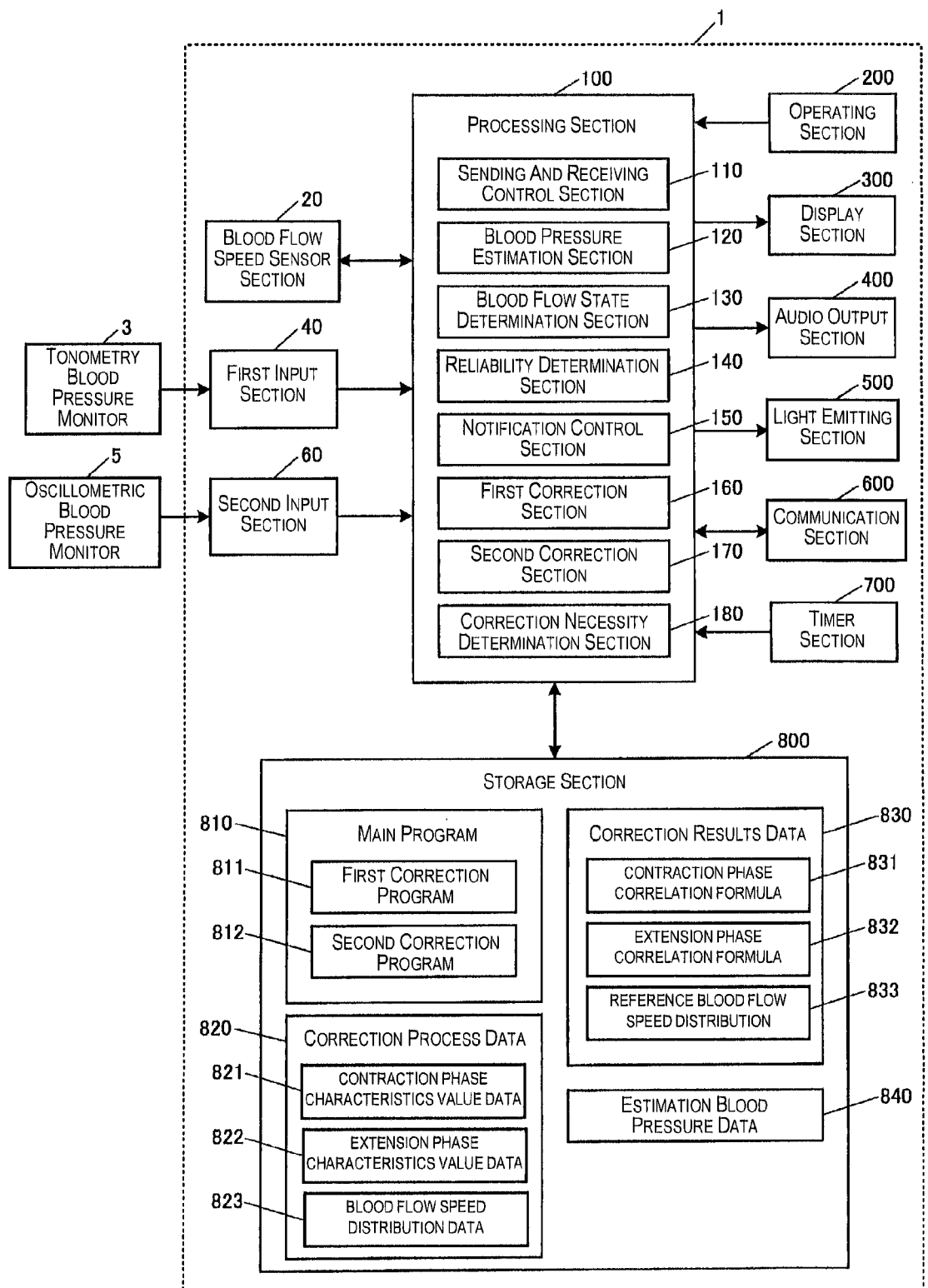
FIG. 4 is a block diagram illustrating an example of a functional configuration of an ultrasound blood pressure monitor.

FIG. 4 is a block diagram illustrating an example of a functional configuration of the ultrasound blood pressure monitor 1. The ultrasound blood pressure monitor 1 is configured to have a processing section 100, the blood flow speed sensor section 20, a first input section 40, a second input section 60, an operating section 200, a display section 300, an audio output section 400, a light emitting section 500, a communication section 600, a timer section 700, and a storage section 800.

The blood flow speed sensor section 20 is a blood flow speed gauging section which gauges the blood flow speed in the measurement target vessel of the patient using ultrasound. The blood flow speed sensor section 20 has an ultrasound oscillation unit array where ultrasound oscillation units are lined up in an array formation, a sending and receiving circuit which controls the sending and receiving of the ultrasound from the ultrasound oscillation units, a Doppler signal extraction circuit which extracts a Doppler shift signal by quadrature detection of a signal which is received using the sending and receiving circuit, a frequency analysis section which performs frequency analysis with regard to the Doppler signal, and the like.

The first input section 40 is an input section which continuously inputs measurement values of the tonometry blood pressure monitor 3 by being connected to the tonometry blood pressure monitor 3.

The tonometry blood pressure monitor 3 is a first external measurement apparatus which performs gauging of blood pressure using a tonometry method which is a type of continuous method. The tonometry method is a method which gauges blood pressure by utilizes that, when a blood vessel wall where the wall is relatively thin is pressurized by a pressure plate with a certain area from the outer side of the skin, a circumference direction response in the wall is eliminated when the blood vessel wall becomes flat and the inner pressure is reflected directly in the pressure plate. The tonometry method has the characteristics such that it is possible to continuously measure a blood pressure waveform for each pulse in a non-invasive manner.

The second input section 60 is an input section which inputs measurement values of the oscillometric blood pressure monitor 5 by being connected to the oscillometric blood pressure monitor 5. Here, the blood pressure which is measured by a measurement unit such as the oscillometric blood pressure monitor 5 can be input according to a user operation without the oscillometric blood pressure monitor 5 being connected.

The oscillometric blood pressure monitor 5 is a second external measurement apparatus which performs gauging of blood pressure using an oscillometric method which is a type of intermittent method. The oscillometric method is a method which measures blood pressure by stopping the flow of blood by pressing the pulse due to a cuff being wound around the upper arm or the like, and after this, determining the pressure pulse wave when the pressing is gradually loosened and the blood begins to flow again.

The processing section 100 is a control apparatus and a computation apparatus which comprehensively controls each section of the ultrasound blood pressure monitor 1 and is configured to have, for example, a microprocessor such as a CPU (Central Processing Unit) or a DSP (Digital Signal Processor), an ASIC (Application Specific Integrated Circuit), and the like.

The processing section 100 has a sending and receiving control section 110, a blood pressure estimation section 120, a blood flow state determination section 130, a reliability determination section 140, a notification control section 150, a first correction section 160, a second correction section 170, and a correction necessity determination section 180 as the main functional sections. Here, in the application of the present invention, it is not necessary the case that all of these functional sections are essential configuration elements, and in addition, functional sections other than these can be essential configuration elements.

The sending and receiving control section 110 controls the gauging of the blood flow speed according to the blood flow speed sensor section 20. Specifically, an ultrasound sending and receiving control signal is output with regard to the blood flow speed sensor section 20 and there is control such that the blood flow speed is gauged using an ultrasound Doppler method by ultrasound being transmitted with regard to the measurement target blood vessel of the patient and a ultrasound reflection wave being received.

The blood pressure estimation section 120 estimates the blood pressure of the patient on the basis of the results of the gauging of the blood flow speed sensor section 20 by referencing the correlation formula (contraction phase correlation formula 831 and extension phase correlation formula 832) which indicates the correlation characteristics of the blood pressure and the blood flow speed of the patient which is stored in correction results data 830 in the storage section 800.

The blood flow state determination section 130 determines the blood flow state of the measurement target blood vessel using the results of the gauging of the blood flow speed sensor section 20. As was described using the principles, for example, the blood flow state determination section 130 determines the blood flow speed distribution in the transverse direction of the measurement target blood vessel as the blood flow state.

The reliability determination section 140 determines the reliability of the blood pressure estimation results according to the blood pressure estimation section 120 by comparing the reference blood flow speed distribution as the reference blood flow state of the measurement target blood vessel which is stored in the correction results data 830 in the storage section 800 and the blood flow speed distribution as the blood flow state which has been determined using the blood flow state determination section 130.

The notification control section 150 performs predetermined notifications based on the determination results of the reliability determination section 140. For example, there is control such that predetermined notifications are performed with regard to the patient via the display section 300, the audio output section 400, and the light emitting section 500. That is, the display section 300, the audio output section 400, and the light emitting section 500 are equivalent to a notification section which performs notification in accordance with control of the notification control section 150.

The first correction section 160 performs a first correction process where the correlation characteristics are corrected by rederiving the correlation characteristics (the correlation formula) using the measurement values which are continuously input using the first input section 40 in accordance with a first correction program 811 which is stored in the storage section 800. The first correction section 160 functions as a correlation characteristics correction section which corrects the correlation characteristics based on the blood pressure which is input by the input section (the first input section 40) and the results of the gauging of the blood flow speed sensor section 20 and as a reference blood flow state updating section which updates the reference blood flow state using the results of the gauging of the blood flow speed sensor section 20 when correcting according to the correlation characteristics correction section.

The second correction section 170 performs a second correction process where the correlation characteristics are corrected by modifying the correlation characteristics (the correlation formula) using the measurement values which are input using the second input section 60 in accordance with a second correction program 812 which is stored in the storage section 800.

The correction necessity determination section 180 determines the necessity of correction by comparing the reference blood flow state of the measurement target blood vessel (for example, the reference blood flow speed distribution) and the blood flow state which is determined by the blood flow state determination section 130 (for example, the blood flow speed distribution).

The operating section 200 is an input apparatus which is configured to have a button switch and the like and a signal of a button which has been pressed is output to the processing section 100. Due to the operation of the operating section 200, the input of various types of instructions such as an instruction for the starting of measurement of blood pressure is carried out. The operating section 200 is equivalent to the operation button 12 in FIG. 1.

The display section 300 is a display apparatus which is configured to have an LCD (Liquid Crystal Display) or the like and performs various types of display based on a display signal which is input from the processing section 100. The estimation results according to the blood pressure estimation section 120 or the like are displayed in the display section 300. The display section 300 is equivalent to the liquid crystal display unit 13 in FIG. 1.

The audio output section 400 is an audio output apparatus which performs various types of audio output based on an audio output signal which is input from the processing section 100. The audio output section 400 is equivalent to the speaker 14 in FIG. 1.

The light emitting section 500 is a light emitting apparatus which emits light in accordance with a light emitting control signal which is input from the processing section 100. The light emitting section 500 is equivalent to the LED lamp 15 in FIG. 1.

The communication section 600 is a communication apparatus for sending and receiving information which is used in the apparatus to and from an external information processing apparatus in accordance with the control of the processing section 100. As the communication method of the communications section 600, it is possible to apply various methods such as a format where a cable which complies with a predetermined communication standard is connected in a wired manner, a format where there is connection via an intermediate apparatus which is also used as a recharger referred to as a cradle, a format where wireless communication is performed using short-distance wireless communication, or the like. The first input section 40 and the second input section 60 becomes the communication section 600 in a case where the connection with the tonometry blood pressure monitor 3 and the oscillometric blood pressure monitor 5 is a communication connection.

The timer section 700 is a timer apparatus which is configured to have a crystal oscillator, which is formed by a crystal resonator and an oscillator circuit, or the like and measures time. The time measuring of the timer section 700 is output at any time to the processing section 100.

The storage section 800 is configured to have a storage apparatus such as a ROM (Read Only Memory), a flash ROM, a RAM (Random Access Memory), or the like. The storage section 800 stores a system program of the ultrasound blood pressure monitor 1, various types of programs for realizing each of the functional sections of the sending and receiving control function and the blood pressure estimation function, data, and the like. In addition, there is a work area which temporarily stores processing data of various types of processing, processing results, and the like.

A main program 810, which is read out by the processing section 100 and is executed as a main process (refer to FIG. 7), is stored in the storage section 800. The main program 810 includes the first correction program 811 which is executed as the first correction process (refer to FIG. 8) and the second correction program 812 which is executed as the second correction process (refer to FIG. 9) as subroutines. These processes will be described later in detail using flow charts.

In addition, correction process data 820, the correction results data 830, and estimation blood pressure data 840 are stored in the storage section 800.

The correction process data 820 is processing data which the processing section 100 uses in the first correction process and contraction phase characteristics value data 821, extension phase characteristics value data 822, and blood flow speed distribution data 823 are included in this.

FIG. 5 is a diagram illustrating an example of the data configuration of the contraction phase characteristics value data 821. Characteristics value numbers 821A and contraction phase characteristics values 821B are stored so as to correspond in the contraction phase characteristics value data 821. Contraction phase blood pressure and contraction phase central blood flow speed are included in the contraction phase characteristics value 821B. The contraction phase central blood flow speed is the blood flow speed contraction phase in the center position "O" of the blood vessel.

In the contraction phase characteristics value data 821, the contraction phase blood pressure which is input from the tonometry blood pressure monitor 3 and the contraction phase central blood flow speed which is gauged by the blood flow speed sensor section 20 are stored as the characteristics values which are measured at the same timing for each pulse in a chronological series to correspond to the characteristic value numbers 821A in the first correction process.

FIG. 6 is a diagram illustrating an example of the data configuration of the extension phase characteristics value data 822. Characteristics value numbers 822A and extension phase characteristics values 822B are stored so as to correspond in the extension phase characteristics value data 822. Extension phase blood pressure and extension phase central blood flow speed are included in the extension phase characteristics value 822B. The extension phase central blood flow speed is the extension phase blood flow speed in the center position "O" of the blood vessel.

In the extension phase characteristics value data 822, the extension phase blood pressure which is input from the tonometry blood pressure monitor 3 and the extension phase central blood flow speed which is gauged by the blood flow speed sensor section 20 are stored as the characteristics values which are measured at the same timing for each pulse in a chronological series to correspond to the characteristic value numbers 822A in the first correction process.

The blood flow speed distribution data 823 is data where the blood flow speed distribution, which is determined using the blood flow state determination section 130 in the first correction, is stored in a chronological series.

The correction results data 830 is data which is found as the results of the first correction process or the second correction process and the contraction phase correlation formula 831, the extension phase correlation formula 832, and the reference blood flow speed distribution 833 are included in this.

The estimation blood pressure data 840 is data where the blood pressure which is estimated according to the blood pressure estimation section 120 is stored in a chronological series.

4. Process Flow

Figure 7:
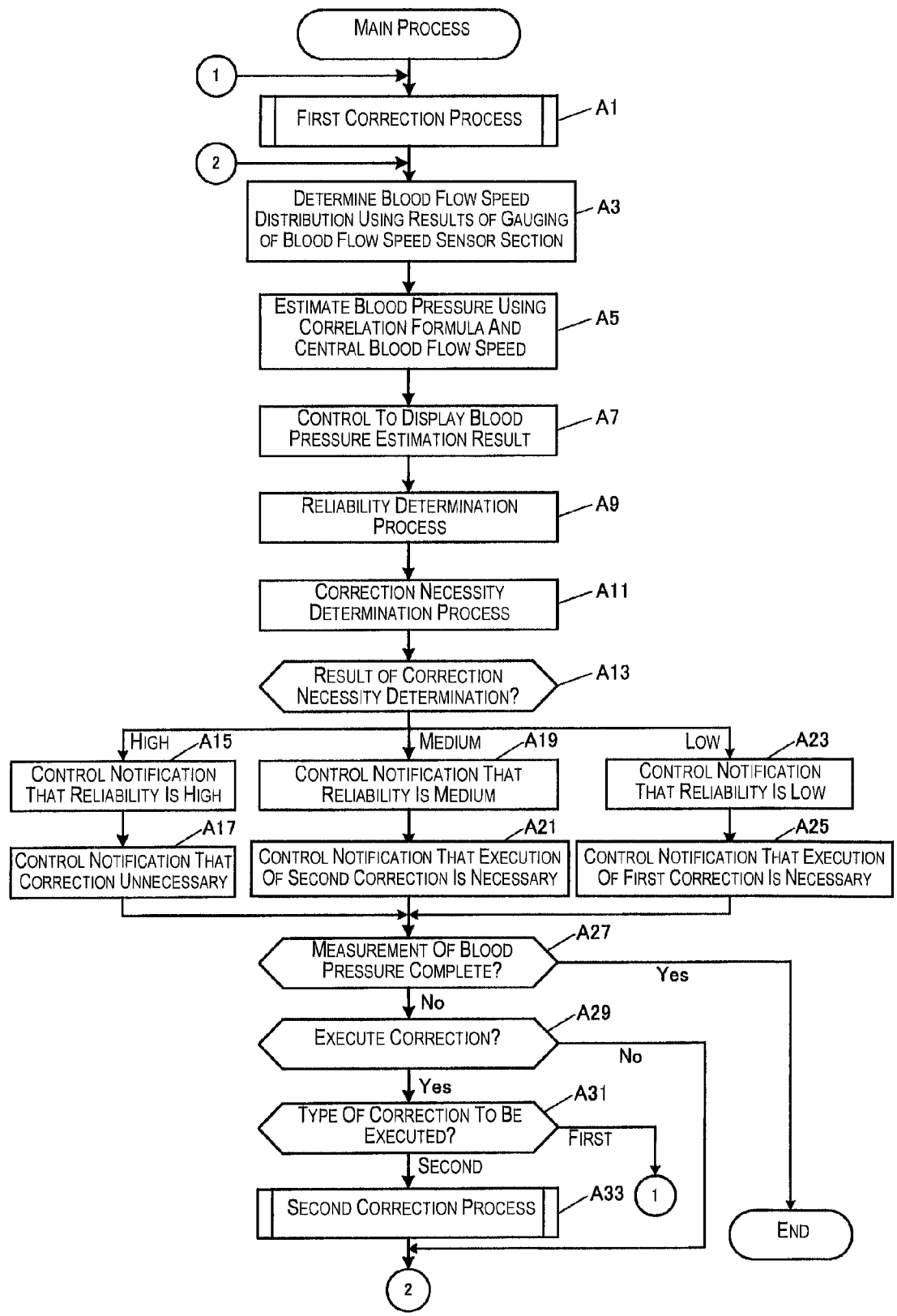
FIG. 7 is a flow chart illustrating a flow of a main process.

FIG. 7 is a flow chart illustrating the flow of the main process which is executed by the processing section 100 in accordance with the main program 810 which is stored in the storage section 800. To begin with, the first correction section 160 performs the first correction process in accordance with the first correction program 811 which is stored in the storage section 800 (step A1).

Figure 8:
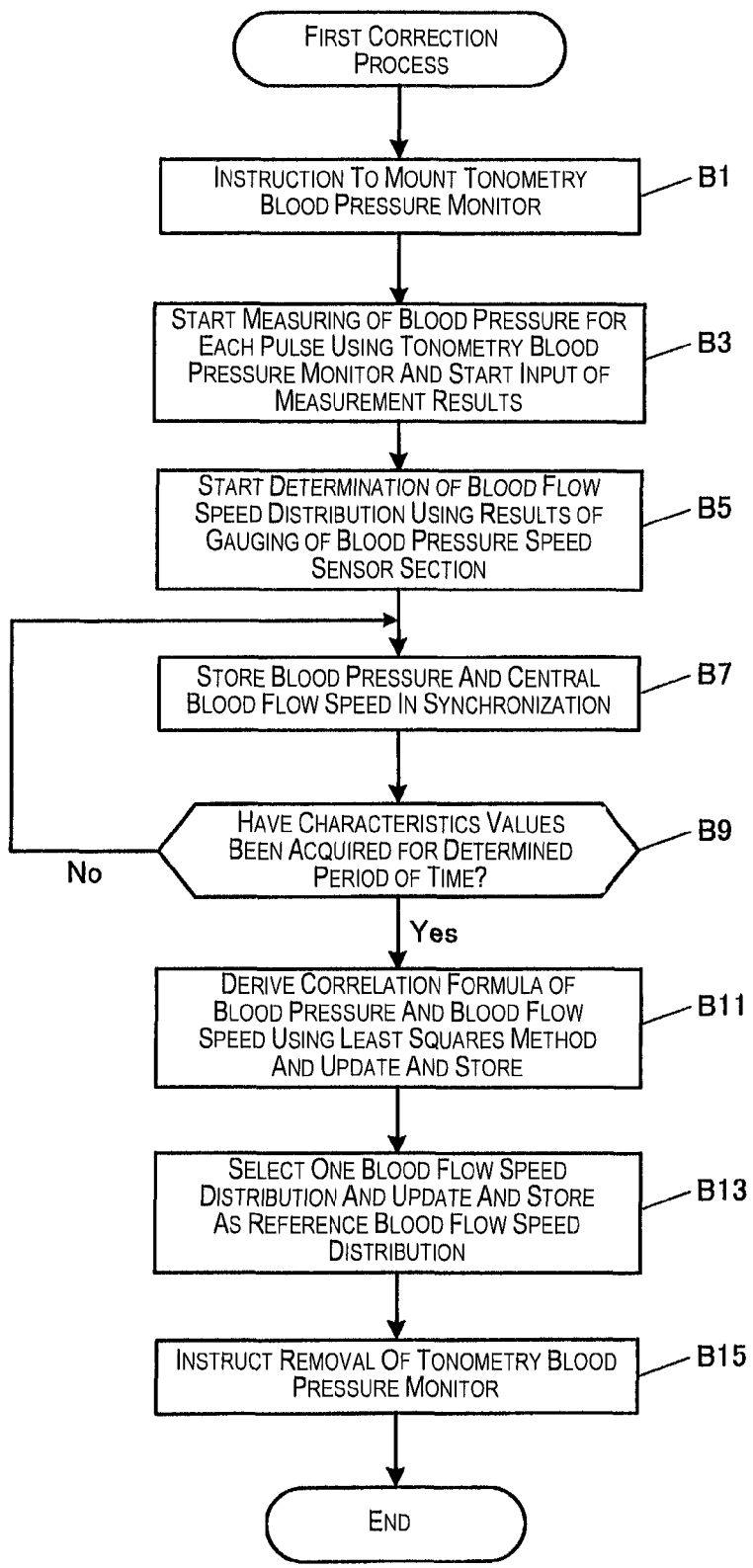
FIG. 8 is a flow chart illustrating a flow of a correction process.

FIG. 8 is a flow chart illustrating the flow of the first correction process. The first correction section 160 performs an instruction to mount the tonometry blood pressure monitor 3 with regard to the patient (step B1). When the tonometry blood pressure monitor 3 and the ultrasound blood pressure monitor 1 are connected and the measurement of blood pressure for each pulse according to the tonometry blood pressure monitor 3 is started, the blood pressure measurement results (the contraction phase blood pressure and the extension phase blood pressure) are input via the first input section 40 (step B3).

On the other hand, the blood flow state determination section 130 starts the determination of the blood flow speed distribution using the results of the gauging of the blood flow speed sensor section 20 and the determination results are stored in the blood flow state distribution data 823 (step B5).

The first correction section 160 stores the blood pressure which is input from the tonometry blood pressure monitor 3 and the central blood flow speed which is found from the results of the gauging of the blood flow speed sensor section 20 in the storage section 800 so as to correspond as data which is synchronized (step B7). That is, the contraction phase blood pressure and the extension phase blood pressure for each pulse which is input from the tonometry blood pressure monitor 3 and the contraction phase central blood flow speed and the extension phase central blood flow speed for each pulse are stored so as to respectively correspond to the contraction phase characteristics value data 821 and the extension phase characteristics value data 822 (step B7).

Next, the first correction section 160 determines whether the characteristics values has been acquired for a predetermined period of time (step B9), and in a case where it is determined that the characteristics values have not yet been acquired (step B9; No), the process returns to step B7. It is possible for the predetermined period of time to be appropriately set, but it is sufficient if the period of time is set such that a sufficient number of characteristics values are acquired such that it is possible to derive the correlation formula with a high degree of precision.

In a case where it is determined that the characteristics values have been acquired for the predetermined period of time (step B9; Yes), the first correction section 160 derives the correlation formula with the blood pressure and the blood flow speed using, for example, a least squares method and updates and stores the correction results data 830 (step B11). That is, the contraction phase correlation formula 831 and the extension phase correlation formula 832 are derived respectively using the contraction phase characteristics value 821 and the extension phase characteristics values 822. In this step, the values of both the slope and the intercept which are the parameters of the correlation formula are calculated.

Next, the first correction section 160 selects one of the blood flow speed distributions from among the blood flow speed distribution data 823 and updates and stores the correction results data 830 as the reference blood flow speed distribution 833 (step B13). Specifically, for example, the reference blood flow speed distribution 833 is updated by one of the blood flow speed distributions, which correspond to the timing where the contraction phase central blood flow speed was observed, being selected from among the blood flow speed distribution data 823.

Then, the first correction section 160 terminates the first correction process after performing a removal instruction for the tonometry blood pressure monitor 3 (step B15).

Returning to the main process of FIG. 7, after the first correction process has been performed, the processing section 100 starts blood pressure estimation in the unit of the ultrasound blood pressure monitor 1. Firstly, the blood flow state determination section 130 determines the blood flow speed distribution using the results of the gauging of the blood flow speed sensor section 20 (step A3).

Then, the blood pressure estimation section 120 estimates the blood pressure (the contraction phase blood pressure and the extension phase blood pressure) using the correlation formula (the contraction phase correlation formula 831 and the extension phase correlation formula 832), which is stored in the correction results data 830 stored in the storage section 800, and the central blood flow speed (the contraction phase central blood flow speed and the extension phase central blood flow speed), which is found from the results of the gauging of the blood flow speed sensor section 20, and stores the estimation results in the estimation blood pressure data 840 in the storage section 800 (step A5). Then, the processing section 100 controls the display of the blood pressure estimation results on the display section 300 (step A7).

Next, the reliability determination section 140 performs a reliability determination process which determines the reliability of the blood pressure estimation results (step A9). In addition, the correction necessity determination section 180 performs a correction necessity determination process which determines whether correction of the correlation formula is necessary (step A11). The content of the processes of the reliability determination method and the correction necessity method are as described above.

After this, the processing section 100 determines the reliability determination results (step A13) and in a case where the reliability determination results are "high" (step A13; high), the notification control section 150 notifies the patient that the reliability of the blood pressure estimation results is high (step A15). For example, an icon which indicates that the reliability of the blood pressure estimation results is high is controlled so as to be displayed on the display section 300. In addition, in combination with this, the notification control section 150 notifies the patient that correction is not necessary (step A17). For example, the LED lamp 15 with a blue color in the light emitting section 500 is controlled so as to flash.

In a case where the reliability determination results are "medium" (step A13; medium), the notification control section 150 notifies the patient that the reliability of the blood pressure estimation results is medium (step A19). For example, an icon which indicates that a small error is included in the blood pressure estimation results is controlled so as to be displayed on the display section 300. In addition, in combination with this, the notification control section 150 performs a notification which prompts the patient to execute the second correction (simple correction) (step A21). For example, the LED lamp 15 with a yellow color in the light emitting section 500 is controlled so as to flash.

In a case where the reliability determination results are "low" (step A13; low), the notification control section 150 notifies the patient that the reliability of the blood pressure estimation results is low (step A23). For example, an icon which indicates that a large error is included in the blood pressure estimation results is controlled so as to be displayed on the display section 300. In addition, in combination with this, the notification control section 150 performs a notification which prompts the patient to execute the first correction (fine correction) (step A25). For example, the LED lamp 15 with a red color in the light emitting section 500 is controlled so as to flash.

Here, it is possible for the notifications in steps A15 to A25 to be realized using notification control with regard to an arbitrary combination of the display section 300, the audio output section 400, and the light emitting section 500 which are the notification section. It is sufficient if notification is performed with regard to the patient by displaying a predetermined message in the display section 300, audio outputting predetermined voice guidance from the audio output section 400, flashing of the LED lamp 15 in the light emitting section 500, or the like.

After steps A17, A21, or A25, the processing section 100 determines whether the measurement of blood pressure is complete (step A27), and in a case where it is determined that the measurement has not yet been completed (step A27; No), it is determined whether correlation is executed (step A29). For example, it is determined whether an instruction operation for the execution of correction has been input by the patient via the operating section 200.

In a case where it is determined that correction is executed (step A29; Yes), the processing section 100 determines whether the second correction has been selected by the patient (step A31). Then, in a case where it is determined that the second correction has been selected (step A31; second), the second correction section 170 performs the second correction in accordance with the second correction program 812 which is stored in the storage section 800 (step A33).

Figure 9:
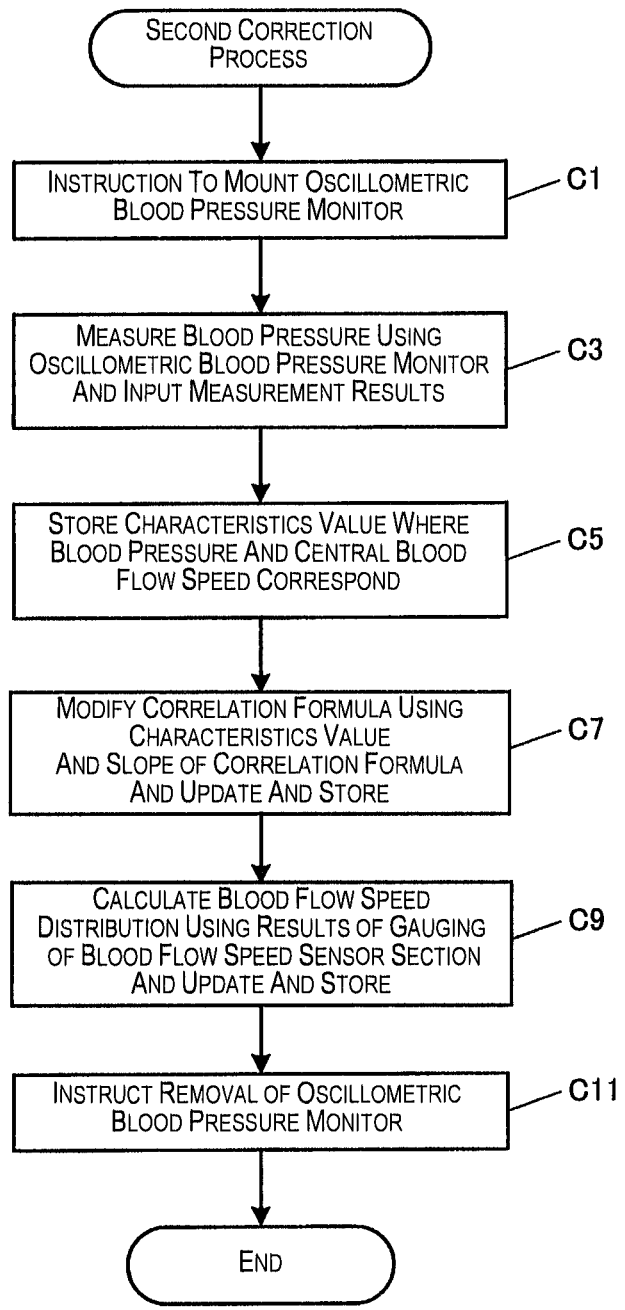
FIG. 9 is a flow chart illustrating a flow of a second correction process.

FIG. 9 is a flow chart illustrating the flow of the second correction process. To begin with, the second correction section 170 performs an instruction to mount the oscillometric blood pressure monitor 5 with regard to the patient (step C1). When the oscillometric blood pressure monitor 5 and the ultrasound blood pressure monitor 1 are connected and the measurement of blood pressure for each pulse according to the oscillometric blood pressure monitor 5 is started, the processing section 100 inputs the blood pressure measurement results (the contraction phase blood pressure and the extension phase blood pressure) via the second input section 60 (step C3).

Next, the second correction section 170 stores the characteristics values, where the blood pressure which is input in step C3 (the contraction phase blood pressure and the extension phase blood pressure) and the central blood flow speed (the contraction phase central blood flow speed and the extension phase central blood flow speed) which is found from the results of the gauging of the blood flow speed sensor section 20 correspond, in the storage section 800 (step C5).

Next, the second correction section 170 modifies the correlation formula using the characteristics value which is found in step C5 and the slope of the correlation formula which is stored in the correction results data 830 and updates and stores the correction results data 830 in the storage section 800 (step C7). That is, the contraction phase correlation formula 831 and the extension phase correlation formula 832 are modified by using a moving average of the correlation formulae so that the slope passes through in the characteristics value as it is respectively with regard to the contraction phase correlation formula 831 and the extension phase correlation formula 832.

After this, the second correction section 170 calculates the blood flow speed distribution using the results of the gauging of the blood flow speed sensor section 20 and updates and stores the reference blood flow speed distribution 833 in the correction results data 830 (step C9). Then, the second correction section 170 terminates the second correction process after performing a removal instruction for the oscillometric blood pressure monitor 5 (step C11).

Returning to the main process in FIG. 7, after the second correction process has been performed or in a case where it is determined that correction is not executed in step A29 (step A29; No), the processing section 100 returns the process to step A3. In a case where the first correction has been selected in step A31 (step A31; first), the processing section 100 returns the process to step A1. In addition, in a case where it is determined that the measurement of blood pressure is complete in step A27 (step A27; Yes), the processing section 100 completes the main process.

5. Action Effects

In the ultrasound blood pressure monitor 1, the blood flow speed in the measurement target blood vessel of the patient is gauged using the blood flow speed sensor section 20. Then, the blood pressure of the patient is estimated using the blood pressure estimation section 120 on the basis of the results of the gauging of the blood flow speed sensor section 20 by referencing the correlation formula (the contraction phase correlation formula 831 and the extension phase correlation formula 832) which is expressed by the correlation characteristics of the blood pressure and the blood flow speed of the patient which was found in the first correction process. As was described using the principles, there is a negative correlation relationship between the blood pressure and the blood flow speed. Accordingly, variation in blood pressure is captured using a simple configuration in which the blood flow speed is gauged using the blood flow speed sensor section 20 by finding the correlation formula of the blood pressure and the blood flow speed of the patient by initially performing the first correction process and it is possible to normally monitor the blood pressure.

However, since the relationship of the blood pressure and the blood flow speed changes over time due to causes such as a change in blood viscosity in the measurement target blood vessel, it is necessary to perform correction of the correlation formula if the blood pressure estimation is to be continuously performed in daily activities. Therefore, there is a configuration with the providing of the first correction section 160, which corrects the correlation formula by rederiving the correlation formula using the measurement values which are continuously input from the tonometry blood pressure monitor 3 which performs gauging of blood pressure using a tonometry method, and the second correction section 170, which corrects the correlation formula by modifying the correlation formula using the measurement values which are directly input from the oscillometric blood pressure monitor 5 which performs gauging of blood pressure using an oscillometric method or the measurement values of the oscillometric blood pressure monitor 5 which are input in accordance with a user operation. Due to this, since it is possible to correct the correlation formula using the measurement values of the external measurement apparatuses which perform gauging of blood pressure using gauging method which are different types, it is possible to correct the correlation formula by appropriately selecting the correction section according to the simplicity of the correction, whether there is an apparatus environment where correction is possible, and the like.

In the first correction process which is performed by the first correction section 160, it is possible to finely perform correction of the correlation formula since the correlation formula is rederived by recalculating the slope and the intercept which are parameters of the correlation formula using the blood pressure which is input from the tonometry blood pressure monitor 3 and the blood pressure and the characteristics values of the blood flow speed for the predetermined period of time which are gauged by the blood flow speed sensor section 20. On the other hand, in the second correction process which is performed by the second correction section 170, it is possible to simplify the correction of the correlation formula since the correlation formula is modified by changing only the intercept without changing the slope of the correlation formula using the blood pressure which is input from the oscillometric blood pressure monitor 5 and one of the characteristics values of the blood flow speed which is gauged by the blood flow speed sensor section 20.

In addition, in the embodiment, the blood flow speed sensor section 20 gauges the blood flow speed at a plurality of positions which are different positions in a diameter direction in the measurement target blood vessel. Then, the blood flow state determination section 130 determines the blood flow speed distribution in the transverse direction of the measurement target blood vessel using the results of the gauging of the blood flow speed sensor section 20 and the correction necessity determination section 180 determines the necessity of correlation of the correlation formula based on the determination results.

The correction necessity determination section 180 determines the necessity of correction of the correlation formula by comparing the undulations (the reference undulations) of the blood flow speed distribution of the reference blood flow state which was found in the first correction process and the undulations (the gauging undulations) of the blood flow speed distribution which has been determined using the blood flow state determination section 130. More specifically, the necessity of correction of the correlation formula is determined based on the difference in the gradient (the reference gradient) of the blood flow speed distribution of the reference blood flow state and the gradient (the gauging gradient) of the blood flow speed distribution which has been determined. When the blood viscosity changes, the difference in the reference gradient and the gauging gradient increases. As a result, it is possible to easily determine the necessity of correction by using the difference in the reference gradient and the gauging gradient as an index for judgment.

In addition, the correction necessity determination section 180 determines whether the correction using any of the first correction section 160 and the second correction section 170 is necessary based on the results of the comparison of the reference undulations and the gauging undulations. In a case where the difference of both is large as a result of the comparison, it is judged that fine correction is necessary and it is determined that correction using the first correction section 160 is necessary. Conversely, in a case where the difference of both is small, it is judged that simple correction is necessary and it is determined that correction using the second correction section 170 is necessary. Due to this, it is possible to appropriately determine whether correction using the first correction section 160 or correction using the second correction section 170 is necessary and to prompt the patient to perform correction according to the determination results.

6. Modified Example

Naturally, the embodiments where it is possible for the present invention to be applied are not limited to the embodiment described above and appropriate changes are possible in a scope which does not depart from the gist of the present invention. Below, modified examples will be described.

6-1. Measurement Target Artery

In the embodiment described above, the measurement target artery is described as the radial artery in the wrist, but naturally, arteries other than this can be the measurement target artery. For example, a limb artery other than the radial artery can be the measurement target artery.

6-2. Method for Measuring Blood Flow Speed

In the embodiment described above, the method for measuring the diameter of blood vessel is described as the measuring method using ultrasound, but naturally, the method for measuring the blood flow speed is not limited to this. For example, a laser Doppler method can be used where the blood flow speed in the measurement target blood vessel is measured by receiving reflected light from the measurement target blood vessel when laser light is irradiated onto the measurement portion and signal processing is carried out.

6-3. Correction Process

In the embodiment described above, there is description where the first correction process is performed after the start of the main process and correction of the correlation formula and correction of the reference blood flow state are performed. However, the following can be carried out without such a configuration being adopted.

The correlation relationship of the blood pressure and the blood flow speed of the patient are set in advance and this is stored in the storage section 800. In the same manner, the reference blood flow state of the measurement target blood vessel is set in advance and this is stored in the storage section 800. After the start of the main process, the blood pressure is estimated by referencing the correction characteristics which are stored in advance in the storage section 800 and the reliability determination and the correction necessity determination are performed using the reference blood flow state which is stored in advance in the storage section 800. Then, correction of the correlation characteristics and updating of the reference blood flow state are performed by executing the correction process at a timing where an operation for the instructing of the execution of the correction process (the first correction process or the second correction process) is carried out by the patient.

6-4. External Measurement Apparatus

In the embodiment described above, there is description where the first external measurement apparatus which performs the gauging of blood pressure using a continuous method is the tonometry blood pressure monitor 3 and the second external measurement apparatus which performs the gauging of blood pressure using an intermittent method is the oscillometric blood pressure monitor 5, but naturally, blood pressure monitors other than these can be used as the external measurement apparatuses. For example, a blood pressure monitor which performs the gauging of blood pressure using a capacity compensation method which is one type of continuous method can be the first external measurement section and a blood pressure monitor using a microphone which performs the gauging of blood pressure using a Korotkoff method which is one type of intermittent method can be the second external measurement apparatus.

6-5. Blood Flow State Determination

The method for determination of the blood flow state of the measurement target blood vessel is not limited to the technique which is described in the embodiment described above and appropriate changes are possible. For example, a curve which indicates changes in the blood flow speed (referred to below as "blood flow speed change curve") is found in an approximate manner from the blood flow speed (the end point of a blood flow speed vector) in each sampling position in the transverse direction of the measurement target blood vessel. Then, the change trend of the blood flow speed can be determined by applying a pattern matching technique with regard to the blood flow speed change curve.

In this case, a plurality of patterns such as a mountain shape, a bowl shape, a bell shape, or a hemispherical shape can be set in advance as the patterns of the change trend of the blood flow speed. Then, the pattern which is most appropriate in the blood flow speed change curve is determined using pattern matching using these patterns. Then, the reliability determination and the correction necessity determination of the embodiment described above are performed based on in what way the pattern of the blood flow speed change curve which has been determined has changed with regard to the pattern of the blood flow speed change curve of the reference blood flow state.

6-6. Reliability Determination Threshold Conditions

The threshold conditions of the reliability determination can be changed in a case where the gauging undulations are large and in a case where the gauging undulations are small compared to the reference undulations. As is understood from FIG. 3, when the blood viscosity in the measurement target blood vessel increases, the gauging undulations are reduced compared to the reference undulations. Therefore, for example, in a case where the gauging undulations are small compared to the reference undulations, the threshold conditions can change such that it is easier to determine when the reliability is low compared to a case where the gauging undulations are large.

For example, it is determined that the reliability of the blood pressure estimation results is low in a case where the absolute value of the different of the reference gradient and the gauging gradient (the gradient difference) exceeds the predetermined threshold. In this case, in a case where the gauging gradient is small compared to the reference gradient, the threshold is set to be lower compared to a case where the gauging gradient is large. By doing this, it is easy for the absolute value of the gradient difference to exceed the threshold, and as a result, it is easy for the reliability of the blood pressure estimation results to be determined as low.

In addition, a case can be considered where the reference undulations (or the reference gradient) which are initially set are where the blood viscosity is high or low to begin with. Also in this case, it is valid if the threshold conditions of the reliability determinations are changed in a case where the gauging undulations are large and a case where the gauging undulations are small compared to the reference undulations.

6-7. Content of Notifications

The content of the notifications which are described in the embodiment described above is only one example, and naturally, appropriate settings and changes are possible. A notification which prompts the execution of correction using the first correction section or the second correction section can be performed in a case where the reliability of the blood pressure estimation results is medium and a notification which prompts the execution of urgent (quick) correction using the first correction section or the second correction section can be performed in a case where the reliability of the blood pressure estimation results is low. In addition, as described below, specific content of the error which is included in the blood pressure estimation results can be notified.

Figure 10:
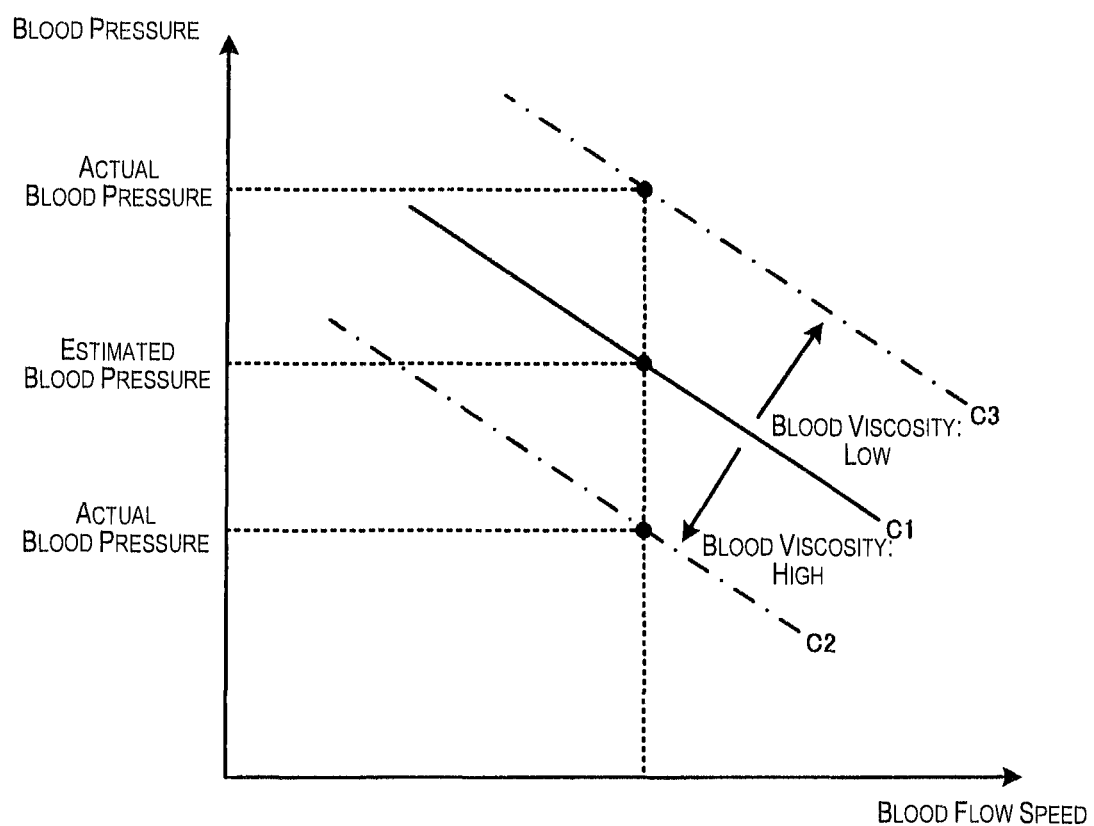
FIG. 10 is a diagram illustrating a relationship of blood viscosity and correlation characteristics.

FIG. 10 is a diagram illustrating a relationship of blood viscosity and correlation characteristics. In FIG. 10, the horizontal axis is blood flow speed and the vertical axis is blood pressure. The line (linear regression line) which is shown as a solid line indicates a correlation formula C1 which is used in the blood pressure estimation. When the blood viscosity changes to be higher compared to during correction, the correlation formula C1 shifts downward and becomes a correlation formula C2 which is shown by a one dot chain line. In this case, blood pressure is estimated to be higher than the actual value of the blood pressure when the blood pressure is estimated using the correlation formula C1. Therefore, in this case, there is notification that a positive error is superimposed on the blood pressure which is displayed in the display section 300.

On the other hand, when the blood viscosity changes to be lower compared to during correction, the correlation formula C1 shifts upward and becomes a correlation formula C3 which is shown by a one dot chain line. In this case, blood pressure is estimated to be lower than the actual value of the blood pressure when the blood pressure is estimated using the correlation formula C1. Therefore, in this case, there is notification that a negative error is superimposed on the blood pressure which is displayed in the display section 300.

6-8. Modification of Correlation Formula

In the embodiment described above, the correlation formula is modified in the second correction process using one point of the characteristics value which is the blood pressure which is input from the oscillometric blood pressure monitor 5 and the blood flow speed which was found from the results of the gauging of the blood flow speed sensor section 20. That is, the correlation formula is modified by using a moving average of the correlation formulae so as to pass through the one point of the characteristics value described above without changing the slope of the correlation formula which was found in the first correction process.

However, the correlation formula can be modified by acquiring not one but a plurality of characteristics values and using these characteristics values and the slope of the correlation formula which was found in the first correction process. In this case, it is sufficient if the correlation formula is modified by performing a regression analysis process with regard to the plurality of characteristics values with the slope of the correlation formula as the value which was found in the first correction process and the intercept of the correlation formula as an unknown value.

6-9. Correlation Characteristics

In the embodiment described above, the case where a linear regression line which is approximated using a linear function is applied as the correlation formula, which is expressed by the characteristic values of the blood pressure and the blood flow speed, is described as an example, but the correlation formula is not limited to this. For example, the correlation formula can be approximated using a non-linear function which has a plurality of three or more parameters. Also in this case, the correlation formula can be rederived by recalculating all of the plurality of parameters of the correlation formula in the first correction process and the correlation formula can be modified by changing a portion of the parameters of the plurality of parameters of the correlation formula in the second correction process.

In addition, it is not necessary for the data of the correlation characteristics which is stored in the storage section 800 to be data of the correlation formula, and naturally, can be data which sets the characteristic values of the blood pressure and the blood flow speed in a table format (a lookup table).

6-10. Average Blood Pressure Estimation

In addition to the configuration of the embodiments described above, the average blood pressure of the contraction phase blood pressure and the contraction phase blood pressure can be estimated. In this case, in the same manner as the embodiment described above, the correlation characteristics of the average blood pressure and the average blood flow speed are corrected by performing the correction process. Then, it is sufficient if the average blood pressure is estimated on the basis of the average blood flow speed which was found from the results of the gauging of the blood flow speed sensor section 20 by referencing the correction characteristics.

The entire disclosure of Japanese Patent Application No. 2011-275359, filed Dec. 16, 2011 is expressly incorporated by reference herein.

What is claimed is:

1. A blood pressure measurement apparatus comprising:
   a sensor configured to gauge blood flow speed in a measurement target blood vessel of a patient;
   a circuit configured to estimate blood pressure on the basis of results of gauging of the sensor by referencing a correlation formula that indicates correlation characteristics of the blood pressure and the blood flow speed of the patient which have been set in advance;
   a first input section including a connector configured to connect a first external measurement apparatus performing blood pressure measurement such that first inputs measurement values that are continuously measured by a continuous method at the first external measurement apparatus are continuously input; and
   a second input section including a connector configured to connect a second external measurement apparatus performing blood pressure measurement such that a second measurement value that is measured by using an intermittent method at the second external measurement apparatus is input;
   the circuit being further configured to correct the correlation formula by rederiving the correlation formula using the first inputs measurement values which are continuously input by the first input section, and to correct the correlation formula by modifying the correlation formula using the second measurement value which is input by the second external input section.

2. The blood pressure measurement apparatus according to claim 1,
   wherein the correlation formula has a plurality of parameters,
   the circuit rederives the correlation characteristics by recalculating all of the values of the plurality of parameters, and modifies the correlation characteristics by changing the values of a portion of the parameters out of the plurality of parameters.

3. The blood pressure measurement apparatus according to claim 1, wherein
   the circuit is further configured to determine the blood flow state of the measurement target blood vessel using the results of the gauging of the blood flow speed, and to determine the necessity of correction of the correlation characteristics by comparing a reference blood flow state of the measurement target blood vessel which is set in advance and the blood flow state which is determined.

4. The blood pressure measurement apparatus according to claim 3,
wherein the circuit is configured to gauge the blood flow speed in a plurality of positions which are different positions in a diameter direction in the measurement target blood vessel, and to determine the distribution or the change trend of the blood flow speed in a transverse direction of the measurement target blood vessel (referred to below comprehensively as "blood flow speed distribution") as the blood flow state using the results of the gauging of the blood flow speed.

5. The blood pressure measurement apparatus according to claim 4,
wherein the circuit is further configured to determine the necessity of correction of the correlation characteristics by comparing the undulations of the blood flow speed distribution of the reference blood flow state (referred to below as "reference undulations") and the undulations of the blood flow speed distribution which is determined (referred to below as "gauging undulations").

6. The blood pressure measurement apparatus according to claim 3,
wherein the circuit is further configured to determine whether the correction is necessary based on the results of the comparison.

7. The blood pressure measurement apparatus according to claim 1, wherein
the correlation formula is a linear function.

8. The blood pressure measurement apparatus according to claim 1, wherein
the correlation formula is a non-linear function.

9. The blood pressure measurement apparatus according to claim 2, wherein
the parameters has at least a first parameter portion and a second parameter portion that is different from the first parameter portion, and the circuit changes a value of the first parameter portion while a value of the second parameter portion is unchanged.

10. The blood pressure measurement apparatus according to claim 3, wherein
the circuit is further configured to determine a necessity of correction of the correlation formula when a difference between the reference blood flow state and the blood flow state is equal to or more than a predetermined threshold, and
to determine a necessity of correction of the correlation formula using the second measurement value, which is different from the correlation formula using the first inputs, measurement values, when the difference between the reference blood flow state and the blood flow state is less than the predetermined threshold.

11. A control method of a blood pressure measurement apparatus comprising:
gauging blood flow speed in a measurement target blood vessel of a patient by a sensor;
estimating blood pressure on the basis of the results of the gauging by referencing a correlation formula that indicates correlation characteristics of the blood pressure and the blood flow speed of the patient which have been set in advance;
inputting continuously continuous measurement values from a first external measurement apparatus that connects the blood pressure measurement apparatus and performs gauging of blood pressure using a continuous method;
inputting an intermittent measurement value from a second external measurement apparatus that connects the blood pressure measurement apparatus and performs gauging of blood pressure using an intermittent method;
correcting the correlation formula by rederiving the correlation characteristics using the continuous measurement values; and
correcting the correlation formula by modifying the correlation characteristics using the intermittent measurement value.

12. A blood pressure measurement apparatus comprising:
a sensor configured to measure blood flow speed in a measurement target blood vessel of a patient;
a first connector configured to connect a circuit to a first external measurement apparatus performing blood pressure measurement such that continuous measurement values that are continuously measured by a continuous method at the first external measurement apparatus are continuously input;
a second connector configured to connect the circuit to a second external measurement apparatus performing blood pressure measurement such that an intermittent measurement value that is measured by using an intermittent method at the second external measurement apparatus is input;
the circuit configured to estimate blood pressure on the basis of the blood flow speed that is measured by the sensor and a correlation formula that indicates correlation characteristics of the blood pressure and the blood flow speed of the patient, the correlation formula being set in advance before the sensor measures the blood flow speed, the circuit being further configured to correct the correlation formula by utilizing both of the continuous measurement values and the intermittent measurement value.

13. A blood pressure measurement method, comprising:
measuring blood flow speed in a measurement target blood vessel of a patient by a sensor;
inputting continuously continuous measurement values from a first external measurement apparatus that is connected to a circuit for estimating blood pressure and performs gauging of blood pressure using a continuous method;
inputting an intermittent measurement value from a second external measurement apparatus that is connected to the circuit for estimating blood pressure and performs gauging of blood pressure using an intermittent method;
estimating blood pressure with the circuit on the basis of the blood flow speed that is measured by the sensor and a correlation formula that indicates correlation characteristics of the blood pressure and the blood flow speed of the patient, the correlation formula being set in advance before the measuring of the blood flow speed; and
correcting the correlation formula by utilizing both of the continuous measurement values and the intermittent measurement value.

* * * * *